United States Patent
Vandenesch et al.

(10) Patent No.: US 9,382,571 B2
(45) Date of Patent: Jul. 5, 2016

(54) **METHOD FOR DETECTING DELTA HAEMOLYSIN OF *STAPHYLOCOCCUS AUREUS* BY MASS SPECTROMETRY DIRECTLY USING A BACTERIAL POPULATION**

(71) Applicants: Francois Vandenesch, Rillieux la Pape (FR); Olivier Dauwalder, Lyons (FR); Jean-Philippe Charrier, Tassin la Demi-Lune (FR); Martin Welker, Berlin (DE)

(72) Inventors: Francois Vandenesch, Rillieux la Pape (FR); Olivier Dauwalder, Lyons (FR); Jean-Philippe Charrier, Tassin la Demi-Lune (FR); Martin Welker, Berlin (DE)

(73) Assignees: BIOMERIEUX, Marcy l'Etoile (FR); HOSPICES CIVILS DE LYON, Lyons (FR); UNIVERSITE CLAUDE BERNARD LYON I, Villeurbanne (FR)

( * ) Notice: Subject to any disclaimer, the term of this patent is extended or adjusted under 35 U.S.C. 154(b) by 264 days.

(21) Appl. No.: 14/355,668
(22) PCT Filed: Nov. 6, 2012
(86) PCT No.: PCT/FR2012/052556
§ 371 (c)(1),
(2) Date: May 1, 2014
(87) PCT Pub. No.: WO2013/068685
PCT Pub. Date: May 16, 2013

(65) Prior Publication Data
US 2015/0004644 A1 Jan. 1, 2015

(30) Foreign Application Priority Data
Nov. 8, 2011 (FR) .................. 11 60176

(51) Int. Cl.
| | |
|---|---|
| G01N 33/569 | (2006.01) |
| C12Q 1/14 | (2006.01) |
| H01J 49/00 | (2006.01) |
| H01J 49/16 | (2006.01) |
| H01J 49/40 | (2006.01) |

(52) U.S. Cl.
CPC ............. *C12Q 1/14* (2013.01); *G01N 2560/00* (2013.01); *H01J 49/004* (2013.01); *H01J 49/164* (2013.01); *H01J 49/40* (2013.01)

(58) Field of Classification Search
CPC ............................. C12Q 1/14; G01N 2560/00
USPC ........................ 436/86–87, 89, 173; 435/36
See application file for complete search history.

(56) References Cited

U.S. PATENT DOCUMENTS

| | | | |
|---|---|---|---|
| 6,908,740 B2 * | 6/2005 | Vandekerckhove | C07K 1/36 435/23 |
| 8,155,892 B2 * | 4/2012 | Nassif | C12Q 1/04 435/91.1 |
| 8,546,082 B2 * | 10/2013 | Hall | C12Q 1/6883 435/6.12 |

(Continued)

OTHER PUBLICATIONS

Du, Z. et al, Analytical Chemistry 2002, 74, 5487-5491.*

(Continued)

*Primary Examiner* — Arlen Soderquist
(74) *Attorney, Agent, or Firm* — Ladas & Parry LLP

(57) ABSTRACT

The present invention relates to a method for studying a sample containing a bacterial population of *Staphylococcus aureus* with a specific mass spectrometry technique allowing specific detection on the obtained mass spectrum of the presence or of the absence of a peak at an m/z value of 3005±5 Th Thomson or at 3035±5 Th Thomson, and accordingly, to the issuance of a decision conditioned by this result.

14 Claims, 3 Drawing Sheets

(56) References Cited

U.S. PATENT DOCUMENTS

| | | | |
|---|---|---|---|
| 8,723,106 B2* | 5/2014 | van Wuijckhuijse | G01N 1/38 250/281 |
| 8,841,118 B2* | 9/2014 | Robinson | C12Q 1/04 435/287.1 |
| 8,911,987 B2* | 12/2014 | Robinson | G01N 35/0099 435/287.1 |
| 2002/0192676 A1* | 12/2002 | Madonna | G01N 33/56911 435/6.16 |
| 2007/0036776 A1* | 2/2007 | Reid | A61K 35/745 424/93.45 |
| 2008/0138808 A1* | 6/2008 | Hall | C12Q 1/689 435/6.15 |
| 2008/0145847 A1* | 6/2008 | Hall | C12Q 1/689 435/6.15 |
| 2008/0146455 A1* | 6/2008 | Hall | C12Q 1/689 506/8 |
| 2010/0116980 A1* | 5/2010 | Nassif | C12Q 1/04 250/282 |
| 2010/0120085 A1* | 5/2010 | Hyman | C12Q 1/04 435/34 |
| 2010/0129857 A1* | 5/2010 | Walsh | C12Q 1/04 435/34 |
| 2010/0203576 A1* | 8/2010 | Curel | C12Q 1/04 435/29 |
| 2010/0291618 A1* | 11/2010 | Robinson | G01N 35/0099 435/34 |
| 2010/0291619 A1* | 11/2010 | Robinson | C12Q 1/04 435/34 |
| 2010/0291669 A1* | 11/2010 | Robinson | G01N 35/0099 435/287.3 |
| 2011/0204220 A1* | 8/2011 | van Wuijckhuijse | G01N 1/38 250/282 |
| 2011/0294158 A1* | 12/2011 | Somaiya | C12Q 1/14 435/34 |
| 2011/0318776 A1* | 12/2011 | Nassif | G01N 33/6851 435/34 |
| 2015/0136972 A1* | 5/2015 | Lasch | G01N 33/569 250/282 |

OTHER PUBLICATIONS

Majcherczyk, P. A. et al, FEMS Microbiology Letters 2006, 255, 233-239.*
Rajakaruna, L. et al, Infection, Genetics and Evolution 2009, 9, 507-513.*
Rezzonico, F. et al, Applied and Environmental Microbiology 2010, 76, 4497-4509.*
Dauwalder, O. et al, Biotribune 2010, 37, 6-11.*
Hinse, D. et al, Systematic and Applied Microbiology 2011, 34, 52-57.*
International Search Report mailed Apr. 9, 2013, corresponding to International Patent Application No. PCT/FR2012/052556.
Somerville G A et al: Synthesis and deformylation of *Staphylococcus aureus*-toxin are linked to tricarboxylic acid cycle activity:, Journal of Bacteriology, vol. 185, No. 22, Oct. 31, 2003, pp. 6686-6694.
Fowler V G et al: "Persistent bacteremia due to methicillin-resistant *Staphyloccus aureus* infection is associated with agr dysfunction and low-level in vitro resistance to thrombin-induced platelet microbicidal protein", Journal of Infectious Diseases, vol. 190, No. 6, Sep. 2004, pp. 1140-1149.
Shah H N et al:"Tracing the transition of methicillin resistance in sub-populations of *Staphylococcus aureus*, using SELDI-TOF mass spectrometry and artificial neural network Analysis", Systematic and Applied Microbiology, vol. 34, No. 1, Nov. 2010, pp. 81-86.
Jackson K A et al: "Optimisation of intact cell MALDI method for fingerprinting of methicillin-resistant *Staphylococcus aureus*", Journal of Microbiological Methods, vol. 62, No. 3, Sep. 1, 2005, pp. 273-284.
Fox K et al: "Speciation of coagulase negative staphylococci, isolated from indoor air, using SDS page gel bands of expressed proteins followed by MALDI TOF MS and MALDI TOF-TOF MS-MS analysis of tryptic peptides", Journal of Microbiological Methods, vol. 84, No. 2, Dec. 2, 2010, pp. 243-250.

Balaban, N. and R. P. Novick (1995). "Translation of RNAIII, the *Staphylococcus aureus* agr regulatory RNA molecule, can be activated by a 3'-end deletion." FEMS Microbiology Letters, 133(1-2): 155-161.
Bittar, F., Z. Ouchenane, et al. (2009). "MALDI-TOF-MS for rapid detection of staphylococcal Panton-Valentine leukocidin." International Journal of Antimicrobial Agents 34(5): 467-470.
Bizzini, A. and G. Greub (2010). "Matrix-assisted laser desorption ionization time-of-flight mass spectrometry, a revolution in clinical microbial identification." Clinical Microbiology and Infection, 16(11): 1614-1619.
Boles, B. R. and A. R. Horswill (2008). "Agr-mediated dispersal of *Staphylococcus aureus* biofilms." PLoS Pathogens, 4(4): e1000052.
Brunskill, E. W. and K. W. Bayles (1996). "Identification and molecular characterization of a putative regulatory locus that affects autolysis in *Staphylococcus aureus*." Journal of Bacteriology, 178(3): 611-618.
Cherkaoui, A., J. Hibbs, et al. (2010). "Comparison of two matrix-assisted laser desorption ionization-time of flight mass spectrometry methods with conventional phenotypic identification for routine identification of bacteria to the species level." Journal of Clinical Microbiology, 48(4): 1169-1175.
Dauwalder O., et al., "Detection of Panton—Valentine toxin in *Staphylococcus aureus* by mass spectrometry directly from colony: time has not yet come." International Journal of Antimicrobial Agents (2010), 36(2): 193-194.
Dufour, P., S. Jarraud, et al. "High genetic variability of the agr locus in *Staphylococcus* species." Journal of Bacteriology (2002), 184(4): 1180-1186.
Edward-Jones, V., M. A. Ciaydon, et al., "Rapid discrimination between methicillin-sensitive and methicillin-resistant *Staphylococcus aureus* by intact cell mass spectrometry." J Med Microbiol (2000), 49(3): 295-300.
Felden, B., F. Vandenesch, et al. "The *Staphylococcus aureus* RNome and its commitment to virulence." PLoS Pathogens (2011), 7(3): e1002006.
Fitton, J. E., A. Dell et al., "The amino acid sequence of the delta haemolysin of *Staphylococcus aureus*." FEBS Letters (1980), 115(2): 209-212.
Goerke, C., S. Campana, et al., "Direct quantitative transcript analysis of the agr regulon of *Staphylococcus aureus* during human infection in comparison to the expression profile in vitro." Infection Immunity (2000) 68(3): 1304-1311.
Hawkins, C., J. Huang, et al. "Persistent *Staphylococcus aureus* bacteremia: an analysis of risk factors and outcomes." Arch Intern Med (2007), 167(17): 1861-1867.
Kornblum, J. S., S. J. Projan, et al. "A rapid method to quantitate non-labeled RNA species in bacterial cells." Gene (1988), 63(1): 75-85.
Kreger, A. S., K. S. Kim, et al. "Purification and properties of staphylococcal delta hemolysin." Infection Immunity (1971), 3(3): 449-465.
Otto, M., "Basis of virulence in community-associated methicillin-resistant *Staphylococcus aureus*." The Annual Review Microbiol(2010), 64:143-162.
Otto, M. and F. Gotz, "Analysis of quorum sensing activity in staphylococci by RP-HPLC of staphylococcal delta-toxin." Biotechniques(2000), 28(6): 1088, 1090, 1092, 1096.
Paizs, B. and S. Suhai, "Fragmentation pathways of protonated peptides." Mass Spectrometry Reviews(2005), 24 (4): 508-548.
Rose, W. E., M. J. Rybak, et al. "Correlation of vancomycin and daptomycin susceptibility in *Staphylococcus aureus* in reference to accessory gene regulator (agr) polymorphism and function." Journal of Antimicrobial Chemotherapy 59(6): 1190-1193 (2007)
Sakoulas, G., G. M. Eliopoulos, et al."Reduced susceptibility of *Staphylococcus aureus* to vancomycin and platelet microbicidal protein correlates with defective autolysis and loss of accessory gene regulator (agr) function." Antimicrobial Agents and Chemotherapy 49(7): 2687-2692 (2005).
Sakoulas, G., G. M. Eliopoulos, et al. "Accessory gene regulator (agr) locus in geographically diverse *Staphylococcus aureus* isolates with reduced susceptibility to vancomycin." Antimicrob Agents Chemother 46(5): 1492-1502 (2002).

(56) References Cited

OTHER PUBLICATIONS

Schweizer, M. L., J. P. Uruno, et al. "Increased mortality with accessory gene regulator (agr) dysfunction in *Staphylococcus aureus* among bacteremic patients." Antimicrobial Agents Chemotherapy, 55(3): 1082-1087 (2011).

Szabados, F., K. Becker, et al., "The matrix-assisted laser desorption/ionisation time-of-flight mass spectrometry (MALDI-TOF MS)-based protein peaks of 4448 and 5302 Da are not associated with the presence of Panton-Valentine leukocidin." International Journal of Medical Microbiology, 301(2011): 58-63.

Tholey, A. and E. Heinzle "Ionic (liquid) matrices for matrix-assisted laser desorption/ionization mass spectrometry—applications and perspectives." Anal Bioanal Chem(2006) 386(1): 24-37.

Traber, K. and R. Novick "A slipped-mispairing mutation in AgrA of laboratory strains and clinical isolates results in delayed activation of agr and failure to translate delta- and alpha-haemolysins." Mol Microbiol 59(5): 1519-1530 (2006).

Traber, K. E., E. Lee, et al. (2008). "agr function in clinical *Staphylococcus aureus* isolates." Microbiology 154(Pt 8): 2265-2274.

Tsuji, B. T., R. D. MacLean, et al. "Impact of accessory gene regulator (agr) dysfunction on vancomycin pharmacodynamics among Canadian community and health-care associated methicillin-resistant *Staphylococcus aureus*." Annals of Clinical Microbiology and Antimicrobials (2011). 10: 20.

Turner, W. H. (1978). "Purification and characterization of an immunologically distinct delta-hemolysin from a canine strain of *Staphylococcus aureus*." Infection and Immunity, 20(2): 485-494.

Verdon, J., N. Girardin, et al. (2009). "delta-hemolysin, an update on a membrane-interacting peptide." Peptides 30(4): 817-823.

Vuong, C., H. L. Saenz, et al. "Impact of the agr quorum-sensing system on adherence to polystyrene in *Staphylococcus aureus*." J Infect Dis 182(6): 1688-1693 (2000).

Welker, M. and E. R. Moore (2011). "Applications of whole-cell matrix-assisted laser-desorption/ionization time-of-flight mass spectrometry in systematic microbiology." Systematic and Applied Microbiology, 34(1): 2-11.

Wertheim, H. F., D. C. Melles, et al. (2005). "The role of nasal carriage in *Staphylococcus aureus* infections." Lancet Infect Dis 5(12): 751-762.

\* cited by examiner

METHOD FOR DETECTING DELTA HAEMOLYSIN OF *STAPHYLOCOCCUS AUREUS* BY MASS SPECTROMETRY DIRECTLY USING A BACTERIAL POPULATION

This application is a 371 of PCT/FR2012/052556, filed on Nov. 6, 2012, which claims priority to French Application No. 1160176, filed Nov. 8, 2011.

The present invention relates to the technical field of analyzing *Staphylococcus aureus* bacteria. Hosted by carriers representing 20 to 30% of the population, *Staphylococcus aureus* is a bacteria responsible for colonizations and infections (Wertheim, Melles et al. 2005). Two great types of infections may be distinguished: suppurative infections involving adhesion factors <<Microbial Surface Component Recognizing Adhesive Matrix Molecules>> or MSCRAMM (the binding protein of fibrinogen [FnBP], protein A, coagulases, etc.); and toxinic infections requiring the secretion of exotoxins, the most notorious of which are hemolysins, Panton-Valentine leukocidin [PVL], staphylococcal enterotoxins and exfoliative toxins (Otto 2010). All the strains of *S. aureus* do not have all the factors of virulences and these factors are not expressed at the same time during bacterial growth. In the exponential growth phase, there is expression of adhesion factors, required for colonization and invasion of the host. Conversely, at the end of the exponential growth phase and during the stationary phase, the bacterium in majority expresses toxins required for destroying the cells of the host, a source of essential nutrients for its growth. *S. aureus* has many regulation factors which will control these processes (Dufour, Jarraud et al. 2002). Among them, the <<Accessory Gene Regulator>> [agr] system is one of the most important systems.

The agr system of *S. aureus* regulates a large number of virulence genes and of the metabolism of the bacterium. It consists in a locus of 5 genes (agrBDCA and hld) distributed in two divergent transcripts: RNA II et RNA III. RNA II is the messenger of the operon P2 which contains the agrBDCA genes; and the RNA III contains hld, the gene of hemolysin Delta [δ]. agrC codes for an histidine kinase and agrA is the receptor of the two-component system. agrD codes for a peptide, which is ripened and secreted by agrB. The resulting peptide is a self-inducer peptide which activates agrC which stimulates agrA. Once it is activated, the agrA receptor induces transcriptions of the RNAs II and RNAs III by means of the respective promoters P2 and P3. The RNA III contains hld, a gene coding for hemolysin δ, but is above all a regulator RNA, a real effector of the agr system. Thus, this RNA III regulates a large number of genes both on a transcriptional and a translational level (Verdon, Girardin et al. 2009; Felden, Vandenesch et al. 2011). Mutations inducing malfunction of the agr system cause modifications in the expression of autolysins and hemolysins; and effects on the bacterial phenotype, notably involved in the pathogenic potential (Schweizer, Furuno et al. 2011).

Hennolysin δ of *S. aureus*, also called δ-toxin or δ-lysin, is coded by the hld gene which belongs to the agr system. It is localized within RNA III, an effector of the agr system. Translation of the RNA III into hemolysin δ is delayed (≠1 hour) and occurs at the end of the exponential growth phase (Balaban and Novick 1995; Somerville, Cockayne et al. 2003). Hennolysin δ is thus the reflection of the transcription of the RNA III, therefore of the functionality of the agr system (Felden, Vandenesch et al. 2011). It belongs to the family of the hemolytic toxins of *S. aureus* and generates pores in the cell membrane. It notably causes lysis of human, rabbit, sheep, horse, cat, chicken erythrocytes etc. by destroying the phospholipids of the cell membranes (Kreger, Kim et al. 1971). It is also involved in preventing the formation of biofilm and in initiating oxidative stress in human neutrophils (Somerville, Cockayne et al. 2003). It consists of 26 amino acids as illustrated in FIG. 1 and has a mass of 2.9 kDa (Fitton, Dell et al. 1980). It appears in two forms: i) N-terminal formylated ob the methionine residue, which is the native and majority form, designated in this document as hemolysin δ; and ii) deformylated (Verdon, Girardin et al. 2009). Deformylation is ensured by an enzyme: an iron-dependent deformylase peptide. During the exponential phase and the early post-exponential phase, hemolysin δ is deformylated in order to obtain a weakly chemo-attracting entity (Somerville, Cockayne et al. 2003). Gradually during bacterial growth, the iron concentration will be reduced, causing a reduction in the activity of the deformylase. There is then an accumulation of hemolysin δ, provided with chemo-attracting properties of neutrophils; and inducing an inflammatory response, source of nutrients for future bacterial growth (Somerville, Cockayne et al. 2003). Finally, polymorphisms have been described: one variant was found in strains of canine origin. It has variations in amino acids; reduced digestion under the action of trypsin; reduced hemolytic potential on sheep red blood cells and reduced hemolytic activity at temperatures below 25° C. (Turner 1978). In strains of human origin, a polymorphism of the type with glycine in position 10 replaced with serine (G10S) is described in the Genebank™ (Figueiredo, Jarraud et al. 2000) but the prevalence of this mutation is not known.

The deficient strains of *S. aureus* for the agr system have a frequency estimated to be between 15% and 22% according to studies (Traber, Lee et al. 2008; Schweizer, Furuno et al. 2011; Tsuji, Maclean et al. 2011). These strains are more frequent among hospital *S. aureus* which are resistant to methicillin [MRSA] as compared with community MRSAs (Tsuji, Maclean et al. 2011). However, deficient strains for agr have been found in all the agr genetic pools: I, II, III and IV, not supporting the clonal assumption (Rose, Rybak et al. 2007).

These strains have real clinical relevance since they are isolated within biological samples having been subject to a minimum of manipulations and are not the result of mutations occurring during successive replantings (Traber, Lee et al. 2008). Different clinical connections have been established between dysfunction of the agr system and the absence of hemolysin δ.

For example, in 2011, a retrospective study conducted between 2003 and 2007 dealing with 814 *S. aureus* bacteremia again found 22% of strains having a dysfunction of the agr system In 18% of the cases, the patient infected by these strains died within 30 days against 12% with strains for which the agr system is functional (p=0.03). thus, an infection by a deficient *S. aureus* strain for agr was capable of predicting mortality with a sensitivity of 30%, a specificity of 79%, a positive predictive value of 18% and a negative predictive value of 88% (Schweizer, Furuno et al. 2011).

Moreover, a retrospective clinical study dealing with persistent bacteremia (BP) with MRSA (i.e. persistence of positive hemocultures with MRSA beyond the 7 days under suitable antibiotherapy) showed that the MRSA strain having a dysfunction of the agr system, objectified by searching for hemolysin δ on gelose, were more frequently found during persistent bacteremia (BP) as compared with resolvent bacteremia (RB) [71.4% of the strains of BP groups versus 38.9% of the strains of the RB group; p=0.057). Thus, the absence of production of hemolysin δ, evidence of the dysfunction of the agr system, may be a marker of persistent bacteremia, requiring increased management (i.e. optimum antibiotherapy) (Fowler, Sakoulas et al. 2004).

A connection with bacterial autolysis has also been established. The agr system controls the expression of many genes notably lytS and lytR. Thus, a dysfunction of the agr system is associated with the formation of aggregates in a liquid medium; alterations of the cell surface, which becomes rough and diffused; and predisposition to autolysis (Brunskill and Bayles 1996).

Vuong et al. as for them, have shown in a model of adhesion to polystyrene that 78% of the agr-deficient strains formed a biofilm versus only 6% of the strains expressing agr. This phenomenon was also confirmed by adding agr inhibitors and seems due to the surfactant properties of hemolysin δ (Vuong, Saenz et al. 2000). However, as much the dysfunction of the agr system is required for generating the biofilm, as much the dispersion of the biofilm seems to be under the dependency of the agr system emphasizing the probable coexistence of deficient strains and of functional strains for the agr system during chronic infections (Boles and Horswill 2008). These accumulated results plead in favor of searching for agr-deficient strains during chronic infections or on intra-vascular devices.

The connection with cystic fibrosis was also established. In 2000, Goerke et al. studied the expression of RNA III in *S. aureus* strains isolated from respiratory samples from patients affected with cystic fibrosis. The predominance of agr-deficient strains was shown. The functionality of the agr system would therefore not be necessary for colonization and infection during cystic fibrosis (Sakoulas, Eliopoulos et al. 2005).

Finally, the connection with the glycopeptide-resistance phenotype (i.e. GISA for <<Glycopeptide Intermediate *Staphylococcus aureus*>>) has also been reported. Prolonged administration (i.e. for more than 9 months) of vancomycin in a patient infected with an MRSA strain having a functional agr system induces a reduction in the expression of hemolysin δ without the latter being completely abolished. Upon stopping the treatment, a notable increase in the expression of hemolysin δ is measured (Sakoulas, Gold et al. 2006). Moreover, the strains having a dysfunction of the agr system show reduced sensitivity to vancomycin, although the pharmacodynamics of the latter is not altered (Tsuji, Maclean et al. 2011). In 2002, Sakoulas et al. demonstrated that the whole of the strains included in the GISA collection of their laboratory had dysfunction of the agr system (Sakoulas, Eliopoulos et al. 2002). In 2005, the connection between the emergence of a hetero GISA phenotype and prolonged exposure to vancomycin of deficient strains of the agr system was confirmed. This reduction of the sensitivity to vancomycin is also associated with a reduction in bacterial lysis and lesser sensitivity to platelet anti-microbial peptides (Sakoulas, Eliopoulos et al. 2005). This association was also confirmed by the study of Rose et al. showing the increased capability of agr-deficient strains of increasing their minimum inhibitory concentrations (MIC) to vancomycin, thus becoming GISA. Conversely, this phenomenon is not found with another anti-*S. aureus* antibiotic belonging to another class of antibiotics: daptomycin (Rose, Rybak et al. 2007). Thus, demonstrating the absence of production of hemolysin δ may be an early marker for detecting a time-dependent change towards the GISA phenotype or the hetero GISA phenotype, in particular during treatment with vancomycin (Fowler, Sakoulas et al. 2004).

Also, considering the clinical interest which is the detection of hemolysin δ, different methods for measuring hemolysin δ of *S. aureus* have been described. Mention may be made of hemolysis tests, biotests on an animal model, <<Reverse Transcription-Polymerase Chain Reaction [RT-PCR]>>, <<Northern blot>>, sequencing and high performance chromatography [HPLC].

In the hemolysis test, hemolysin δ may be detected by measuring the hemolysis induced by an *S. aureus* strain cultivated on gelose to the blood in the presence of anti-hemolysin Alpha [α] and Beta [β] antibodies. Hemolysin δ may also be detected by searching for hemolysis synergy between hemolysin δ and hemolysin β (Verdon, Girardin et al. 2009). Different methodologies were described: Sakoulas et al. detect hemolysin δ by using the RN4420 *S. aureus* strain producing a large hemolysis area in use by hemolysin β. A derived methodology has also been described by Schweitzer et al. These methods are easy to conduct but require the carrying out of a <<dedicated>> test and have a subjective readout: search for hemolysis synergy, which is sometimes difficult to observe. Finally these tests may be marred with false negatives as compared with <<Northern Blot>> and with the sequencing of the agr gene (Traber, Lee et al. 2008).

Historically, biotests on an animal model have also been used. In this case, the activity of hemolysin δ may be detected by the measurements of the minimum lethal dose [MLD] on mice or guinea pigs. It however requires large doses (mouse MLD=110 mg/kg and guinea pig MLD=30 mg/kg). Another methodology consists of investigating the capability of hemolysin δ of inducing cutaneous necrosis in rabbits. About 1 mg of hemolysin δ induces, 24 hours later, wide erythema (diameter>28 mm) and induration followed at D+3 by a necrotic area. Desquamation may also be observed, at a smaller dose (Kreger, Kim et al. 1971).

The expression of hemolysin δ may also be evaluated by RT-PCR targeting RNA III. Total RNA is extracted from a strain and competitive RT-PCR is conducted. In order to normalize the results, Goerke et al. have used the housekeeping gene coding for the gyrase (gyr), the expression of which is constant regardless of the growth phases. RNA III RT-PCR represents a sensitive, specific and quantitative technique. However, its use is reserved for specialized laboratories because of a high risk of contamination (Goerke, Campana et al. 2000).

The expression of hemolysin δ may be indirectly detected by using a <<Northern Blot>> targeting RNA III (Kornblum, Projan et al. 1988; Goerke, Campana et al. 2000; Traber and Novick 2006).

Certain authors have also used the complete sequencing of the agr locus for identifying point-like mutations which may explain its dysfunction (Traber and Novick 2006).

Several HPLC techniques have also been used. In 2000, Otto and Gotz described a qualitative and quantitative method for measuring hemolysin δ by high performance liquid chromatography (HPLC). The supernatants of bacterial cultures made in a trypticase soy bean broth are centrifuged at 19,000 g for 5 minutes. The supernatants are then analyzed by HPLC on a PHE (<<Phenyl derivated>>) column of 1 mL and then eluated with a gradient of 10 to 90% of solvent B, the solvent A being a 0.1% trifluoroacetic acid [TFA]/water mixture and the solvent B being a 0.1% TFA/acetonitrile mixture. The detection is achieved with a UV spectrometer with 214 or 280 nm diode bars (Otto and Gotz 2000). In 2002, Somerville et al. as for them described a methodology close to the one of Otto and Gotz for detecting and measuring hemolysin δ with HPLC but coupled with detection by mass spectrometry with an electrospray source. They thereby obtained a m/z of 3007 Thomson [Th] and 2972 Th for native and deformylated forms of hemolysin δ (Somerville, Cockayne et al. 2003).

In this context, the inventors focused on a novel method for studying colonies of *Staphylococcus aureus* which gives the possibility of issuing a diagnostic and/or establishing a link with the presence or the absence of hemolysin δ. This method should be fast and easy to use, and notably not require any burdensome steps for extracting proteins.

The present invention relates to a method for studying a sample containing a bacterial population of *Staphylococcus aureus* with a mass spectrometry technique comprising the following steps:

a) positioning the sample in contact with the medium allowing ionization by action of a laser beam, of the molecules present in the sample, b) ionizing the molecules present in the sample by means of a laser beam, c) accelerating the obtained ionized molecules by a potential difference, d) letting the ionized and accelerated molecules freely move in at least one tube under reduced pressure, e) detecting at least one portion of the ionized and accelerated molecules which have freely moved, so as to measure the time which they take for covering at least one tube under reduced pressure and obtaining a signal corresponding to a number of ionized molecules detected at a given instant, f) calculating the mass over charge ratio [m/z] of the detected molecules so as to obtain a signal corresponding to the number of ionized molecules of a same mass over charge ratio [m/z], depending on the m/z ratio of the detected molecules, g) determining either directly or indirectly, if, among the ionized molecules obtained in step b), there were or not ionized molecules with a mass/charge [m/z] equal to 3005±5 Th or equal to 3035±5 Th, h) issuing a decision conditioned by the result obtained in step g).

According to a first alternative embodiment, step h) corresponds to a correlation step of the absence of both ionized molecules with an m/z equal to 3005±5 Th and of ionized molecules of m/z equal to 3035±5 Th with the absence of hemolysin δ and of its variant G10S in the analyzed bacterial population of *Staphylococcus aureus*.

Hemolysin δ of sequence SEQ ID NO. 1: XaaAQDIIS-TIGDLVKWIIDTVNKFTKK, with Xaa=methionine formulated in the N-terminal position, has a protonated single isotope mass (MH$^+$) of 3005, 6 Th.

Its variant with a sequence SEQ ID NO. 2: XaaAQDIIS-TISDLVKWIIDTVNKFTKK, with Xaa=methionine formulated in the N-terminal position, has a protonated single isotope mass (MH$^+$) of 3035, 6 Th.

According to a second alternative embodiment, step h) corresponds to a step for correlating the absence of both ionized molecules of m/z equal to 3005±5 Th and ionized molecules of m/z equal to 3035±5 Th with dysfunction of the agr system (<<Accessory Gene Regulator>>) in the analyzed bacterial population of *Staphylococcus aureus*.

According to a third alternative embodiment, the analyzed bacterial population of *Staphylococcus aureus* comes from a biological sample from a patient and step h) corresponds to a step for correlating the absence of both ionized molecules with m/z equal to 3005±5 Th and ionized molecules of m/z equal to 3035±5 Th with issuance for said patient of a clinical diagnostic known to be related to dysfunction of the agr system.

According to a fourth alternative embodiment, the analyzed bacterial population of *Staphylococcus aureus* comes from a biological sample of a patient and step h) corresponds to a step for correlating the absence of both ionized molecules with m/z equal to 3005±5 Th and ionized molecules with m/z equal to 3035±5 Th with the diagnostic of a chronic infection in a patient. A chronic infection is defined on the basis of the clinic-biological criterion consisting of finding the isolation, up to 6 months before, of a strain of *S. aureus* having the same antibiogram as the isolated strain during the study. As examples of such chronic infections, mention may be made of osteo-articular infections, chronic diabetic foot infections, infections on an implantable vascular device.

According to a fifth alternative embodiment, step h) corresponds to a step for correlating the absence of both ionized molecules of m/z equal to 3005±5 Th and ionized molecules of m/z equal to 3035±5 Th with a classification of the analyzed *Staphylococcus aureus* bacterial population as having the risk of exhibiting reduced sensitivity to glycopeptides (i.e. GISA).

The sample on which the method of the invention may be applied may be of biological origin, notably animal or human origin. It may then correspond to a sample of biological fluid, for example full blood, serum, plasma, urine, cerebro-spinal fluid, organic secretion, to a tissue sample or to isolated cells. This sample may be used as such, or else it may be subject before the study, to a preparation of the enrichment or culture type, according to methods known to one skilled in the art.

Within the scope of the invention, the sample to be studied corresponds to a cell medium comprising a bacterial population and not to one or more proteins obtained after an extraction or purification step. Preferably, the studied sample contains a bacterial population, i.e. it contains at least 10 bacteria.

The detection may notably be carried out from a broth of a bacterial culture, stemming from a biological sample, or from a hemoculture. Most often, the mass spectrum is obtained from a sample obtained from a bacterial culture on gelose.

The cell medium is suspended directly in or on the matrix. Such a technique is known under the name of mass spectrometry on whole cells (WC-MS, for <<whole-cell mass spectrometry>>) and may be conducted without any prior, tedious and time-consuming extraction procedure. This technique has already been widely used in the past for bacterial identification, but its use in the case of protein identification is very limited, considering the complexity of the sample. In the majority of the cases, assigning the proteins corresponding to the profile as obtained by WC-MS is unknown or ambiguous. the protein profiles leading to bacterial identification are only compared without the protein composition of these profiles (i.e. the correspondence between peak and protein) being known (Welker and Moore 2011). However, certain authors have proposed the use of this methodology for detecting biomarkers and/or virulence factors involved in bacterial pathogenesis (Bizzini and Greub 2010). For *S. aureus*, certain authors have shown that it is possible to differentiate the MRSAs from MSSAs. However, the collection of strains used was limited (n=10 strains) and required the use of preliminary procedures for preparing the samples (i.e. chemical and mechanical extractions) (Edwards-Jones, Claydon et al. 2000). Other authors have stated that it is possible to detect PVL of *S. aureus* (Bittar, Ouchenane et al. 2009). However, these results prove to be non-specific and were probably the reflection of belonging to a same clone of the collection of the analyzed strains (Dauwalder, Carbonnelle et al. 2010; Szabados, Becker et al. 2011).

Within the scope of the invention, the inventors have thus demonstrated in a totally unexpected way that the presence on the mass spectrum obtained of a peak with the value of m/z equal to 3005±5 Th or at 3035±5 Th, and the absence of peaks both at 3005±5 Th and at 3035±5 Th, may be respectively correlated with the presence and with the absence of hemolysin δ or of its variant, and therefore did not give the possibility of issuing a clinical diagnostic.

Preferably, within the scope of the method according to the invention, regardless of the applied alternatives, mass spectrometry is advantageously conducted on a sample containing a population from 10 to $10^9$ bacteria and preferably $10^5$ to $10^6$ bacteria. The number of bacteria will be assimilated with the counted numbers of Colony Forming Units (CFU) if the sample subject to mass spectrometry was deposited on a standard gelose culture medium for growing *Staphylococcus aureus* after incubation for 18-48 hours at 35±2° C.

In a general way, any matrix-assisted desorption-ionization mass spectrometry method with measurement of the time of flight may be used within the scope of the invention.

According to a particular embodiment, the mass spectrometry used is Matrix Assisted Laser Desorption and Ionization/Time of Flight (MALDI-TOF) <<Mass Spectrometry>> (MS), which notably has the advantage of relatively simple application.

According to another particular embodiment, the mass spectrometry used is MALDI-TOF-TOF tandem MS, which has two successive separations depending on the time of flight and which notably has the advantage of having very good specificity.

Prior to its ionization, the sample is preferentially put into contact with a matrix.

The matrix used advantageously contains a compound selected from 3,5-dimethoxy-4-hydroxycinnamic acid (i.e. sinapic acid or sinapinic acid); α-cyano-4-hydroxycinnamic acid (i.e. alpha-cyano, alpha-matrix or CHCA) ferulic acid and 2,5-dihydroxybenzoic acid (i.e. DHB).

There exist several deposition techniques which may be used in the scope of the invention for putting the sample in contact with the matrix: deposition on a dry matrix layer, a so-called <<thin layer>>, deposition, deposition with a matrix drop, a so-called <<dried drop>> deposition, deposition on a matrix layer, and then adding a matrix drop a so-called <<sandwich>> deposition.

Generally, the matrixes are photosensitive and crystallized in the presence of the sample while preserving the integrity of the molecules. Such matrixes, notably adapted to the MS MALDI-TOF, are well known and selected from: 3,5-dimethoxy-4-hydroxycinnamic acid; α-cyano-4-hydroxycinnamic acid, ferulic acid and 2,5-dihydroxybenzoic acid. Many other compounds are known to one skilled in the art. There even exists liquid matrices which neither crystallize at atmospheric pressure, nor even in vacuo (Tholey and Heinzle 2006). Any other compound which will allow ionization of the molecules of the sample under the effect of a laser beam may be used. Notably, the target, i.e. the support on which the sample is deposited, may directly play the role of a matrix, like in the case of the <<Nano-Assisted Laser Desorption/Ionization>> (NALDI) or <<Desorption/Ionization On Silicon>> (DIOS) techniques. The laser beam may have any type of wavelength promoting sublimation or vaporization of the matrix. Preferably the ultraviolet or even infrared wavelength will be used.

In the matrix, such a compound is put into solution, the most often with water, preferably of <<ultrapure>> quality, or in a water/organics solvent(s) mixture. As an example of conventionally used organic solvents, mention may be made of acetone, acetonitrile, methanol or ethanol. trifluoroacetic acid (TFA) may sometimes be added. A matrix example for example consists of 20 mg/mL of sinapic acid in an acetonitrile/water/TFA 50/50/0.1 (v/v) mixture. The organic solvent allows the hydrophobic molecules present in the sample to dissolve in the solution, while water allows dissolution of hydrophilic molecules. The presence of an acid such as TFA, promotes ionization of the molecules of the sample by capture of a proton (H+).

Preferentially, the sample is deposited on a support called a target, most often in the form of spots. The matrix may be directly deposited on the sample and is then mixed with the latter.

Optionally, the method according to the invention further contains before step b), a step for crystallization of the matrix on or in which the molecules of the sample are adsorbed.

Most often, a crystallization matrix is obtained by letting the matrix dry in or on which the sample has been deposited.

According to a particular embodiment, the medium with which the sample is put into contact corresponds to a matrix adapted to MALDI MS, deposited on a target, and the method comprises before step b), the obtaining of crystallization of the matrix on or in which the molecules of the sample are adsorbed. In this case, the matrix preferentially contains a compound selected from 3,5-dimethoxy-4-hydroxycinnamic acid, α-cyano-4-hydroxycinnamic acid, ferulic acid and 2,5-dihydroxybenzoic acid.

The sample may have been cultivated beforehand in a broth or on a gelose so as to enrich it with bacteria of *Staphylococcus aureus*. Such media, with gelose or as a broth are well known to one skilled in the art. For example mention may be made of gelose with (horse or sheep) blood; Columbia gelose; Polyvitex® <<chocolate>> gelose; ChromID Staph® a chromogenic gelose for searching for *S. aureus* from bioMerieux, etc. The enrichment on the gelose is particularly favorable because it gives the possibility of obtaining pure colonies of *S. aureus* which may be deposited on the target. The solvent present in the matrix is then vaporized, for example, by leaving the sample at a temperature for example belonging to the range from 17 to 30° C., and notably at room temperature (22° C.) for a few minutes for example for 5 minutes to 2 hours. This vaporization of the solvent allows crystallization of the matrix in which the sample is distributed. Next, the sample, placed within the crystallized matrix is subject to mild ionization. This ionization will preferably be achieved with a nitrogen laser emitting a UV beam at 337.1 nm.

During ionization, the sample is subject to excitation by a laser. The crystals of the matrix then absorb the photon energy and release of this energy causes sublimation of the matrix, desorption of the sample and appearance of material in a state described as a plasma. Within this plasma, charge exchanges occur between matrix and sample molecules. For example, protons may be detached from the matrix and transferred to proteins and to peptides of the sample. This step allows mild ionization of the biomolecules without increasing their destruction. The samples thus release ions of different sizes. The latter are then accelerated with an electric field and freely fly in a tube under reduced pressure, called a flight tube. The pressure applied during the ionization and during acceleration of the generated ions most often belongs to the range ranging from $10^{-6}$ to $10^{-9}$ millibars [mbar]. The smallest ions will then <<travel>> more rapidly than the bigger ions thereby allowing their separations. At the terminal end of the flight tube is located a detector. The Time of Flight (or TOF) taken by the ions is used for calculating their mass. Thus, a mass spectrum is obtained, representing the intensity of the signal corresponding to the number of ionized molecules of a same mass over charge ratio [m/z], depending on the m/z ratio of the molecules inpinging the detector. The mass over charge ratio [m/z] is expressed in Thomsons [Th]. Once introduced into the mass spectrometer, the spectrum of a sample is obtained very rapidly, most often in less than one minute.

The fact that the analyzed sample actually contains *Staphylococcus aureus* bacteria may be determined by a test prior to MALDI-TOF MS or concomitantly by means of the MALDI-TOF MS spectrum. In this case, the total MALDI-TOF MS spectrum, which most often comprises between 70 and 200 peaks, will be compared with a spectral database which gives the possibility of determining whether the analyzed bacterial population actually corresponds to *Staphylococcus aureus*. This comparison is based on the use of different algorithms depending on suppliers, and leads to obtaining bacterial identification (Cherkaoui, Hibbs et al. 2010; Welker and Moore 2011).

All the embodiments detailed above are applicable regardless of the mass spectrometry technique used, in particular of the MALDI-TOF or MALDI-TOF-TOF type.

When the mass spectrometry used is MALDI-TOF MS, the determination of step g) is preferably directly inferred from the presence on the mass spectrum obtained of a peak with a m/z value equal to 3005±5 Th or 3035±5 Th or from the absence of peaks both at 3005±5 Th and at 3035±5 Th.

When the mass spectrometry used is MALDI-TOF-TOF MS, the ionized molecules are preferably left to move in a first tube under reduced pressure in step d), the ions of mass m/z equal to 3005±5 Th and/or of mass m/z equal to 3035±5 Th are selected, the ionized molecules are again accelerated after their fragmentation, for example by collision, and the either fragmented or not, ionized molecules are left to freely move in a second tube.

With MALDI-TOF-TOF MS, the determination of step g) is preferably indirectly inferred from the presence of at least five fragments, and preferably of at least 10 fragments, from among the following y and b ion fragments:

the ion fragments y of mass 147.113, 275.208, 376.255, 523.324, 651.419, 765.462, 864.530, 965.578, 1080.605, 1193.689, 1306.773, 1492.852, 1620.947, 1720.016, 1833.100, 1948.127, 2005.148, 2118.232, 2219.280, 2306.312, 2419.396, 2532.480, 2647.507, 2775.565, 2846.603 and 2976.635, with a tolerance of ±1.5 Th; and ion fragments b of mass 131.040, 202.077, 330.136, 445.163, 558.247, 671.331, 758.363, 859.410, 972.494, 1029.516, 1144.543, 1257.627, 1356.695, 1484.790, 1670.870, 1783.954, 1897.038, 2012.065, 2113.112, 2212.181, 2326.224, 2454.319, 2601.387, 2702.435, 2830.530 and 2958.625, with a tolerance of ±1.5 Th, for the peak at 3005±5 Th, and/or the ion fragments y of mass 147.113, 275.208, 376.255, 523.324, 651.419, 765.462, 864.530, 965.578, 1080.605, 1193.689, 1306.773, 1492.852, 1620.947, 1720.016, 1833.100, 1948.127, 2035.159, 2148.243, 2249.290, 2336.322, 2449.406, 2562.491, 2677.517, 2805.576, 2876.613 and 3006.646, with a tolerance of ±1.5 Th; and the ion fragments b of mass 131.040, 202.077, 330.136, 445.163, 558.247, 671.331, 758.363, 859.410, 972.494, 1059.526, 1174.553, 1287.638, 1386.706, 1514.801, 1700.880, 1813.964, 1927.048, 2042.075, 2143.123, 2242.191, 2356.234, 2484.329, 2631.398, 2732.445, 2860.540 and 2988.635, with a tolerance of ±1.5 Th, for the peak at 3035±5 Th.

A method for MALDI-TOF mass spectrometry which may be used according to the invention may notably comprise the following successive steps for obtaining the mass spectrum:

Placing the sample to be studied at the surface or in a matrix suitable for mass spectrometry with desorption-ionization assisted on a matrix per time of flight, Obtaining crystallization of the matrix on or in which the molecules of the sample are adsorbed, Ionizing the crystallized matrix/sample mixture by means of a laser beam, Accelerating the obtained ionized molecules by means of a potential difference, Letting the ionized and accelerated molecules freely move in a tube under reduced pressure, Detecting the ionized molecules at the outlet of the tube, so as to measure the time which they took for covering the tube under reduced pressure and obtaining a signal corresponding to the number of ionized molecules attaining the detector at a given instant, Calculating the mass over charge ratio [m/z] of the detected molecules, so as to obtain a signal corresponding to the number of ionized molecules of a same mass over charge ratio [m/z], depending on the m/z ratio of the detected molecules.

Generally, the calculation of the m/z ratio is obtained, by taking into account the preliminary calibration of the mass spectrometer used, in the form of an equation relating the mass over charge ratio [m/z] and the time of flight in the tube under reduced pressure of the ionized molecules.

MALDI-TOF MS which may be used within the scope of the invention is based on the measurement of the time for traveling from one point A to one point B of ions of different charges and of different masses exposed to an electric field. The measurement of this travel time is dependent on the mass and on the charge of the ion, thereby allowing its separation (Welker and Moore 2011).

A MALDI-TOF-TOF method which may also be used within the scope of the invention may notably comprise the following steps for obtaining the mass spectrum:

Placing the sample to be studied at the surface or in a matrix suitable for MALDI-TOF-TOF MS, Obtaining crystallization of the matrix on or in which the molecules of the sample are adsorbed, Ionizing the sample/crystallized matrix mixture by means of a laser beam, Accelerating the obtained ionized molecules by means of a potential difference, Letting the ionized and accelerated molecules freely move in a first tube under reduced pressure, At the end of the crossing of the first tube, selecting the ionized molecules having the mass of the molecular ions to be fragmented and removing all the other ions, for example by means of an electrostatic deflector, Obtaining fragmentation of the ionized molecules, optionally by causing it by means of an inert gas, Again increasing the potential for causing acceleration of the ionized molecules, for example by means of potential grids so as to give different kinetic energies to the fragment ions and to the precursor ions, Letting the ionized molecules, either fragmented or not, move freely in a second tube under reduced pressure, Detecting the ionized molecules at the outlet of the tube, so as to measure the time which they took for covering the tube under reduced pressure and for obtaining a signal corresponding to the number of ionized molecules attaining the detector at a given instant, Calculating the mass over charge ratio [m/z] of the detected molecules, so as to obtain a signal corresponding to the number of ionized molecules of a same mass over charge ratio [m/s], depending on the m/z ratio of the detected molecules.

Generally, the calculation of the m/z ratio is obtained, by taking into account the preliminary calibration of the mass spectrometer used, in the form of an equation relating the mass over charge ratio [m/z] and the travel time in the tube under reduced pressure of the ionized molecules. The mass of the precursor ions may be used for achieving this calibration.

Any type of MALDI-TOF or MALDI-TOF/TOF mass spectrometer may be used for elaborating the mass spectrum. Such spectrometers comprise:

i) an ionization source (generally a UV laser) intended for ionizing the sample/matrix mixture;
ii) an accelerator for ionized molecules by applying a potential difference,
iii) a tube under reduced pressure in which move the ionized and accelerated molecules,
iv) a mass analyzer intended to separate the formed molecular ions, according to their mass over charge ratio (m/z);
v) a detector intended for measuring the signal directly produced by the molecular ions.

A MALDI-TOF-TOF mass spectrometer is identical with a MALDI-TOF spectrometer with the only difference that the tube under reduced pressure is split into two portions located in the extension of each other (also called here a first tube and second tube under reduced pressure). This geometry allows two successive separations of the molecular ions according to the time of flight: the first allows selection of a molecular ion which will be separated into fragments in the second portion of the tube. By fragment is meant any molecular structure obtained by breaking the selected molecular ions.

The fragmentation of the ions may be obtained either during the initial ionization, or in a collision cell located between the two portions mentioned above of the tube. During the initial ionization, the fragmentation may be directly caused by the energy of the laser beam absorbed by the molecules or be caused by the collision between neutral or ionized molecules in the molecular plasma. If the fragmentation occurred before the phase for accelerating the ions, the fragments migrate according to their respective masses. If it occurs during the acceleration phase, the separation of the so-called metastable ions is poor. If it occurs after the initial acceleration, the fragment ions and their ionized parent molecule (precursor ion) have the same kinetic energy and migrate at the same velocity. This latter type of fragmentation, designated as post-source fragmentation, is utilized in the MALDI-TOF-TOF MS technique. The first portion of the tube (or further designated here as a first tube under reduced pressure) gives the possibility of selecting a window of masses including the mass of the precursor ion of interest and limited by a mass delta. The precursor ion and its fragment are then again accelerated between the two portions of the tube under reduced pressure. The ions then acquire kinetic energy which depends on their mass. They finally migrate into the second portion of the tube under reduced pressure (or further designated here as second tube under reduced pressure) according to their respective masses. It is thus possible to detect the whole of the generated fragments for a given precursor ion.

An alternative of this method consists of adding in the collision cell an inert gas, such as argon, between both portions of the tube under reduced pressure. The ionized molecules then fragment while colliding with the inert gas. They may then be accelerated and separated as earlier.

A MALDI TOF/TOF MS fragments proteins in a preferred way around the peptide bond, it essentially generates ions of type b and of type y according to the usual nomenclature (Paizs and Suhai 2005). Other fragments are also possible, immonium ions, fragment a, etc.

The skilled practitioner has the habit of using the fragmentation profile for generating information on the amino acid sequence of the protein and for trying to identify the protein sequence. He/she notably uses for this purpose software packages such as Mascot from Matrix Science (London, United Kingdom).

Thus, hemolysin δ of SEQ ID NO. 1 will in majority lead:
to the ion fragments y of mass 147.113, 275.208, 376.255, 523.324, 651.419, 765.462, 864.530, 965.578, 1080.605, 1193.689, 1306.773, 1492.852, 1620.947, 1720.016, 1833.100, 1948.127, 2005.148, 2118.232, 2219.280, 2306.312, 2419.396, 2532.480, 2647.507, 2775.565, 2846.603 and 2976.635;
to the ion fragments b of mass 131.040, 202.077, 330.136, 445.163, 558.247, 671.331, 758.363, 859.410, 972.494, 1029.516, 1144.543, 1257.627, 1356.695, 1484.790, 1670.870, 1783.954, 1897.038, 2012.065, 2113.112, 2212.181, 2326.224, 2454.319, 2601.387, 2702.435, 2830.530 and 2958.625.

Also, the hemolysin δ G10S of SEQ ID NO. 2 will in majority lead:
to the ion fragments y of mass 147.113, 275.208, 376.255, 523.324, 651.419, 765.462, 864.530, 965.578, 1080.605, 1193.689, 1306.773, 1492.852, 1620.947, 1720.016, 1833.100, 1948.127, 2035.159, 2148.243, 2249.290, 2336.322, 2449.406, 2562.491, 2677.517, 2805.576, 2876.613 and 3006.646;
and to ion fragments b of mass 131.040, 202.077, 330.136, 445.163, 558.247, 671.331, 758.363, 859.410, 972.494, 1059.526, 1174.553, 1287.638, 1386.706, 1514.801, 1700.880, 1813.964, 1927.048, 2042.075, 2143.123, 2242.191, 2356.234, 2484.329, 2631.398, 2732.445, 2860.540 and 2988.635.

The examples, in connection with the appended figures, hereafter allow illustration of the invention but have no limiting nature.

Figure 3:
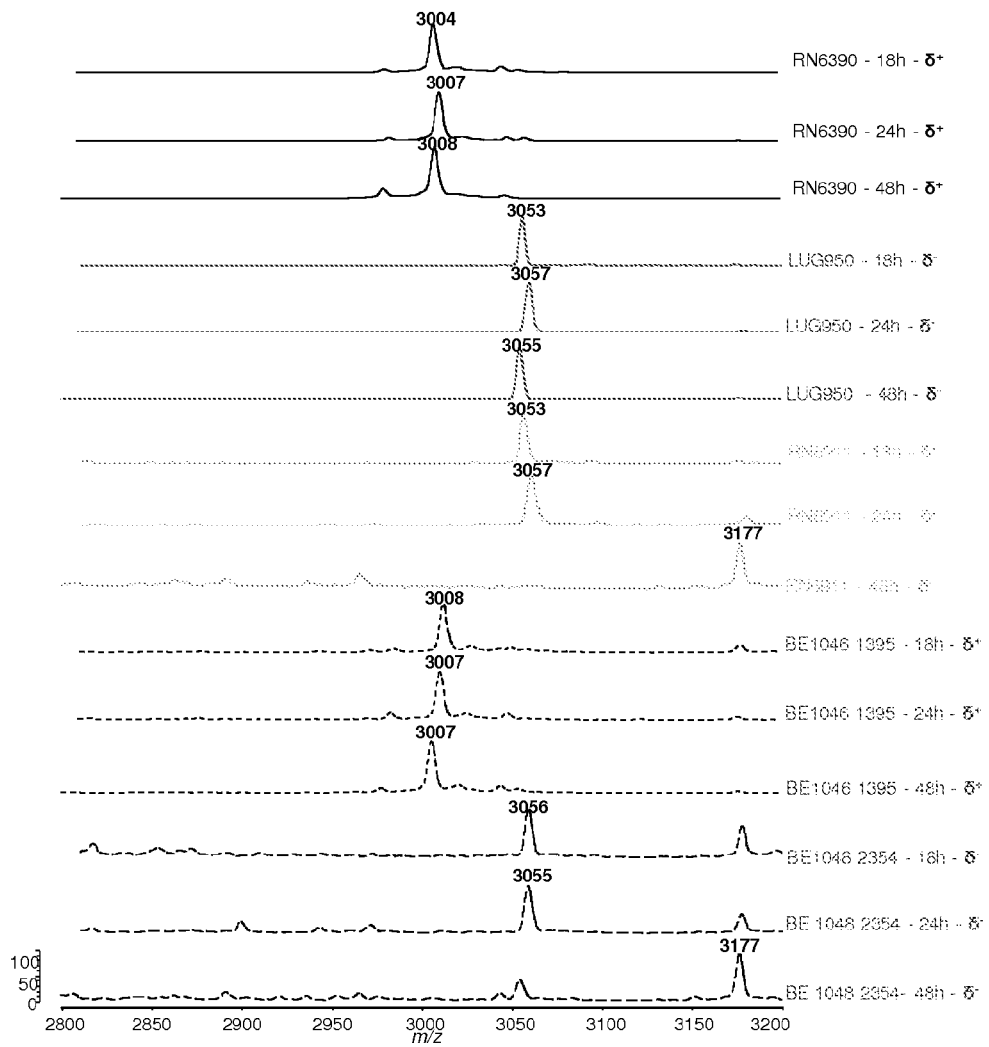

FIG. 3 studies the effect of the culture period (18 to 48 h) on the detection of hemolysin δ with MALDI TOF MS of 3 isogenic strains and of 2 clinical strains.

Figure 4:
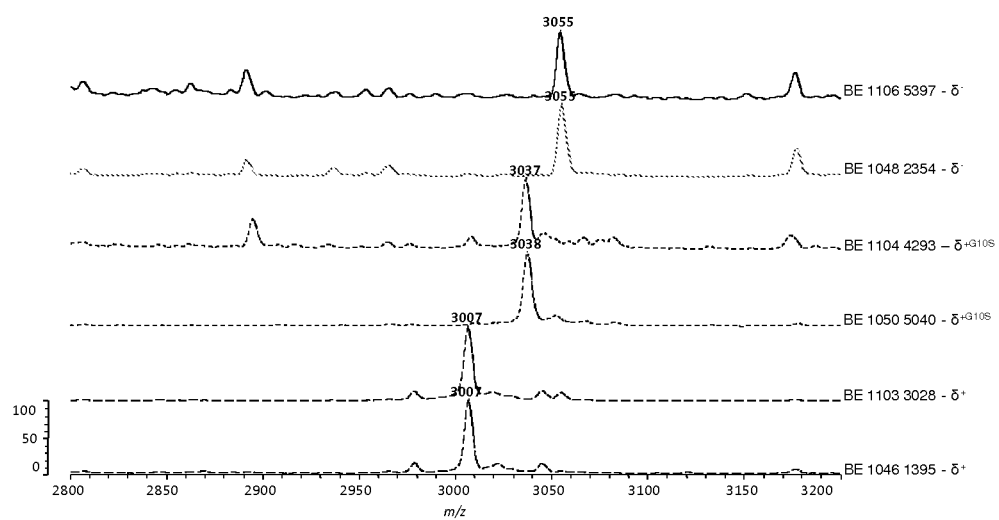

FIG. 4 illustrates the detection of hemolysin δ and of its variant G10S with MALDI TOF MS from clinical strains of *Staphylococcus aureus*.

EXAMPLES

1. Equipment

Matrix

Use of an α-cyano-4-hydroxy cinnamic acid [CHCA] matrix ready to use (Reference 411071, bioMérieux, Marcy l'Etoile, France).

Targets and Internal Control

Use of disposable targets Vitek MS DS® (Reference 410893 bioMérieux, Marcy l'Etoile, France). Use of an ATCC 8739 *Escherichia coli* strain at each analysis allowing calibration and checking of the validity of the calibration of the mass spectrometer.

Type of Deposits

The strains of *Staphylococcus aureus* are deposited in the form of a thin smear of a colony spike (smear in the form of a thin layer). This smear is dried for 5 to 15 minutes at room temperature. One microliter of CHCA matrix is then deposited and then dried for about 5 to 15 minutes at room temperature.

MALDI TOF Mass Spectrometer

Use of a mass spectrometer of the MALDI TOF type, model Axima Assurance® from Shimadzu, Champs sur Marne, France.

Parameterization Used During the Analysis on a MALDI TOF Mass Spectrometer

During analysis of the strains of S. aureus, the following adjustment parameters of the mass spectrometer were used:
  Detection area of the masses: 2,000-20,000 Th
  Power of the laser: 80 volts
  Frequency of the laser: 50 Hertz
  Type of laser: $N_2$
  Mass spectrometer mode: linear, positive,
  Extraction power: 8330 Th
  Activated <<self-quality>> mode
  Minimum intensity: 10 mV
  Minimum signal-to-noise ratio: 10
  Minimum acceptable resolution: 300
  Number of hits: 5 hits/profiles
  Number of profiles per spectrum: 100

Software Packages

The plate plans are made by means of Sirweb-Maldi-Tof® version 11 software package (I2A, Peyrols, France) or Target Manager® version 1.12 software package (bioMérieux, Marcy l'Etoile, France). The mass spectrometer is driven by the LaunchPad® version 2.8.4.20081127 software package (Shimadzu, Champs sur Marne, France).

2. Methodology

Preanalytical Parameters

Analysis of the strains after subculture for 18 to 24 hours on gelose with horse blood (TSH, Reference 43061 bioMérieux, Marcy l'Etoile, France) at 35±2° C. under an aerobic atmosphere.

Initial calibration (additional to the one used for bacterial identification) of the mass spectrometer in the area from 2,800 to 3,200 m/z by means of a calibration standard for mass spectrometry consisting of polyethylene glycol (PEG) 3000.

Analytical Parameters

From a colony spike, producing the deposit on a disposable target according to the <<smear technique>> systematically used during identification of bacteria.

Drying for 5-15 minutes at room temperature.

Adding 1 μL of CHCA matrix over the previous deposit.

Drying for 5-15 minutes.

Producing the <<plate plan>> by means of the Sirweb-Maldi-Tof® or Target Manager® software package.

Starting analysis with MALDI TOF MS by means of the Launchpad® software package for controlling the mass spectrometer Axima Assurance®.

3. Results a. Validation of the Detection i. Use of Isogenic Strains of *Staphylococcus aureus*

Figure 1:
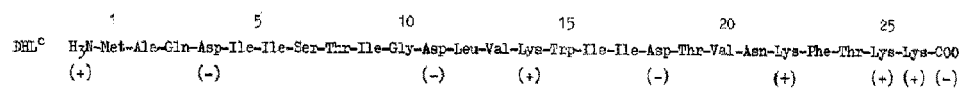
FIG. 1 illustrates the primary sequence of hemolysin δ (Fitton, Dell et al. 1980).
Figure 2:
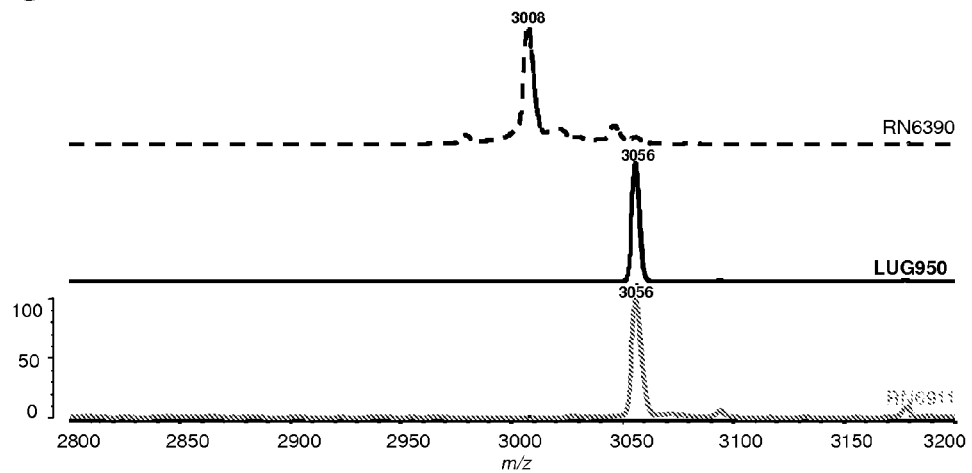
FIG. 2 shows the detection of hemolysin δ with MALDI TOF MS from isogenic strains of *Staphylococcus aureus*.

Analysis of isogenic strains for the agr/rnaIII/hld system obtained by allelic replacement of the agr locus gave the possibility of demonstrating the presence of a peak at 3005±5 Th for strains having a functional agr system. Conversely, isogenic strains identical with the previous parent strains except for a mutated agr system, did not have any peak at 3005±5 Th. The tested RN6390 strain has a functional agr system and is a producer of hemolysin δ; the strain LUG950 is derived from the RN6390 strain in which the gene coding for the RNAIII was invalidated: the strain is deficient for the synthesis of hemolysin δ; the RN6911 strain is a strain obtained by complete deletion of the agr locus (RNA II and RNA III) of the RN6390 strain: the strain is deficient for the synthesis of hemolysin δ. Table I and FIG. 2 summarize the obtained results. FIG. 2 shows the WC MALDI-TOF MS mass spectrum obtained with the three tested strains for m/z ratios comprised between 2,800 and 3,200.

TABLE I

Detection of hemolysin δ with WC-MALDI TOF MS and by investigating hemolysis in a gelose medium on a collection of isogenic strains

| Strain reference | Characteristics | Hemolysis synergy tests on gelose with blood | Presence of a peak at 3005 ± 5 Th |
|---|---|---|---|
| RN6390 | Agr⁺ parent strain | + | + |
| LUG 950 | RN6390 ΔrnaIII | − | − |
| RN 6911 | RN6390 Δagr | − | − | ii. Intermediate Repeatability and Precision Data

In order to be able to do without too strict cultivation conditions required for a use of this detection in daily practice, intermediate repeatability and precision data were established. For this purpose the three isogenic strains described earlier were used (i.e. RN6390; LUG 950; and RN 6911) and 2 clinical strains, one expressing hemolysin δ (i.e. BE1046 1395), the other not (i.e. BE1048 1354). These strains were cultivated for 18, 24 and 48 hours on geloses with horse blood (TSH, Reference 43061, bioMérieux Marcy l'Etoile, France). These strains were then tested in duplicate with WC-MS MALDI TOF MS. In every case, and in all culture times, the peak at 3005±5 Th was detected in all the strains producing hemolysin δ and proves to be absent from the strains having a dysfunction of the agr system (FIG. 3).

iii. Influence of the Culture Media on the Detection of Hemolysin δ

The influence of the culture media was also evaluated. The 5 same strains (the 3 isogenic strains and the 2 clinical strains, one expressing hemolysin δ, the other not), were cultivated on 5 different media for 24 h at 35±2° C. under aerobic conditions: gelose with horse blood (TSH, Reference 43061, bioMérieux, Marcy l'Etoile, France); Columbia gelose (COS, Reference 43041, bioMérieux, Marcy l'Etoile, France); <<chocolate>> gelose (PVX, Reference 43101, bioMérieux, Marcy l'Etoile, France); gelose P (GP, Bacto-Peptone DIFCO®, Becton Dickinson, Pont de Claix, France); and chromogenic gelose for searching for *S. aureus* (ChromID Staph®, Reference 43371, bioMérieux, Marcy l'Etoile, France). These different cultivation conditions do not have any influence on the detection of hemolysin δ with WC-MALDI TOF MS by means of the peak at 3005±5 Th as this appears in Table II.

TABLE II

Influence of the cultivation conditions on the detection of hemolysin δ.

| Strain | TSH ® | COS ® | PVX ® | GP | ChromID Staph ® |
|---|---|---|---|---|---|
| RN6390 | + | + | + | + | + |
| LUG 950 | − | − | − | − | − |
| RN 6911 | − | − | − | − | − |

TABLE II-continued

Influence of the cultivation conditions on the detection of hemolysin δ.

| Strain | TSH ® | COS ® | PVX ® | GP | ChromID Staph ® |
|---|---|---|---|---|---|
| BE10482354 | − | − | − | − | − |
| BE10461395 | + | + | + | + | + |

+: peak at 3005 ± 5 Th detected.
−: absence of any peak at 3005 ± 5 Th.

iv. Prospective Analysis of a Collection of Clinical Strains from the Microbiology Laboratory of the <<Centre De Biologie et Pathologie Est Des Hospices Civils de Lyon>>.

In order to study the clinical impact of the dysfunction of the agr system, objectivied by the absence of the peak of 3005±5 Th, a collection of 168 isolates was prospectively collected between November 2010 and March 2011 in the Bacteriology Laboratory of the <<Centre de Biologie et Pathologie Est>> [CPBE] des Hospices Civils de Lyon [HCL]. From among these, 139 (82.7%) had, in WC-MALDI TOF MS, a peak at 3005±5 Th; 12 (7.2%) had a peak at 3035±5 Th and not at 3005±5 Th; and finally 17 strains (10.1%) did not exhibit any peak at 3005±5 Th, or any peak at 3035±5 Th. In order to confirm the results obtained by a second methodology, hemolysis tests on gelose with blood were conducted. The 17 strains did not show any peak at 3005±5 Th and at 3035±5 Th and did not show any hemolysis. Conversely, the 10 strains without any peaks at 3005±5 Th but having a peak at 3035±5 Th had a positive hemolysis test. Finally, the detection of hemolysin δ by hemolysis test on 5 of the 139 strains taken randomly and having a peak at 3005±5 Th proved to be positive. In order to explain the presence of hemolysis associated with a peak at 3035±5 Th without any peak at 3005±5 Th, the gene hld coding for hemolysin δ was sequenced. For the 10 strains, a mutation causing substitution of glycine with a serine in position 10 (i.e. G10S) was detected, which explains the modification of mass measured by MALDI TOF MS (FIG. 4). Among the strains for which the WC-MALDI TOF MS spectrum for an m/z ratio comprised between 2,800 and 3,200 is illustrated in FIG. 4, the strains BE1046 1395 and BE1103 3028 produce hemolysin δ in a wild form ($\delta^+$); the strains BE1050 5040 and BE1104 4293 produce hemolysin δ having the G10S mutation ($\delta^{+G10S}$); the strains BE1106 5397 and BE1048 2354 are deficient in hemolysin δ ($\delta^-$).

v. MALDI TOF/TOF Analysis

An analysis by <<MALDI-TOF/Time Of Flight>> mass spectrometry [MALDI TOF-TOF MS] on 9 strains was carried out: the 3 isogenic strains described earlier (i.e. RN6390; LUG 950; and RN 6911), 2 non-hemolytic clinical strains having neither a peak at 3005±5 Th nor a peak at 3035±5 Th, 2 hemolytic clinical strains showing a peak at 3005±5 Th; and two hemolytic clinical strains having a peak at 3035±5 Th but without any peak at 3005±5 Th.

Thus, the analysis in the MALDI-TOF-TOF mode of the peak at 3005±5 Th of the RN6390 strain gave the possibility of detecting fragments of hemolysin δ with masses of 147.252, 201.359, 275.471, 330.459, 376.514, 446.482, 523.633, 559.574, 651.7, 672.606, 757.71, 765.841, 864.832, 965.922, 1080.95, 1194.071, 1307.149, 1356.133, 1493.23, 1621.321, 1672.21, 1720.294, 1785.044, 1833.275, 1948.428, 2005.551, 2119.576, 2219.583, 2307.544, 2420.56, 2533.786, 2600.009, 2602.657, 2647.743, 2774.373, 2776.851 and 2975.308 Th. These fragments respectively correspond to the ions y1, y2, y3, y4, y5, y6, y7, y8, y9, y10, y11, y12, y13, y14, y15, y16, y17, y18, y19, y20, y21, y22, y23, y24, y26, b2, b3, b4, b5, b6, b7, b13, b15, b16 and b23 of hemolysin δ of sequence SEQ ID NO. 1 with a tolerance of ±1.5 Th. More than 5 fragments belonging to the hemolysin δ of sequence SEQ ID NO. 1 were thus detected.

Also, the analysis in a MALDI-TOF-TOF mode of the peak at 3035±5 Th of the BE1050 5040 strain gave the possibility of detecting fragments of the hemolysin δ G10S of masses 275.408, 330.363, 376.414, 446.463, 523.39, 559.462, 651.572, 757.505, 765.682, 860.673, 864.661, 965.714, 1080.77, 1175.788, 1193.829, 1306.922, 1493.064, 1621.166, 1701.34, 1720.251, 1814.587, 1833.381, 1948.485, 2035.545, 2148.557, 2249.99, 2336.585, 2449.681, 2562.833, 2677.454 and 2677.935 Th. These fragments respectively correspond to the ions y2, y3, y4, y5, y6, y7, y8, y9, y10, y11, y12, y13, y14, y15, y16, y17, y18, y19, y20, y21, y22, y23, b3, b4, b5, b7, b8, b11, b15 and b16 de hemolysin δ G10S of sequence SEQ ID NO. 2 with a tolerance of ±1.5 Th. More than 5 fragments belonging to the hemolysin δ of SEQ ID NO. 2 were thus detected.

Conversely, MALDI-TOF-TOF analysis of the peak 3053±5 Th of the strain LUG 950 did not allow detection of mass fragments corresponding to SEQ ID NO. 1 or SEQ ID NO. 2. Only the following mass peaks were detected: 72.826, 96.485, 128.727, 214.235, 242.298, 263.249, 267.247, 285.276, 362.359, 476.458, 1206.984 and 1848.786 Th.

In every case, the analysis by MALDI TOF-TOF mass spectrometry and the search in the database Mascott® (Matrix Science Ltd, London, UK) confirmed the totality of the results obtained previously, notably the correspondence of the peak at 3035±5 Th with the mutated form of hemolysin δ G10S.

These examples give the possibility of showing that the MALDI-TOF mode, although simpler to apply, leads to the same identifications as the MALDI-TOF-TOF mode which is more specific.

The totality of the obtained results is summarized in Table III.

TABLE III

Detection of hemolysin δ by MALDI TOF mass spectrometry in 168 clinical strains and correlation with hemolysis synergy tests in diffusion and detection by MALDI TOF/TOF spectrometry.

| | Peak at 3005 ± 5 Th (Number of positive strains/number of analyzed strains) | Peak at 3035 ± 5 Th (Number of positive strains/number of analyzed strains) | Absence of peaks at 3005 ± 5 Th and 3035 ± 5 Th (Number of positive strains/number of analyzed strains) |
|---|---|---|---|
| MALDI TOF | 141/168 | 10/168 | 17/168 |
| Hemolysis synergy test on gelose with blood | 5/5 | 10/10 | 0/17 |
| MALDI TOF/TOF | 2/2 | 2/2 | 0/2 |

Finally, in order to be protected from any biases due to inclusion of strains belonging to a same clone, the 17 strains deficient in hemolysin δ were analyzed with gene chips (IDENTIBAC®, Alere, France), showing that they belong to 4 clonal complexes and to 3 different genetic pools.

vi. Link with Chronicity of the Infection.

In parallel with the collection of the 168 isolates, clinical information relating to the acute versus chronic nature of the infection or of the colonization with S. aureus was collected.

A chronic infection is defined on the basis of the clinic-biological criterion consisting of finding the isolation, up to 6 months previously, of an S. aureus strain having the same antibiogram than the isolated strain during the study. In all the other cases, the infection or the colonization were categorized as acute. Moreover, the presence of implantable pieces of equipment: catheters, osteo-articular or vascular prostheses: frequently found as associated with chronic infections (Hawkins, Huang et al. 2007), was also collected.

On 34 strains isolated during chronic infections, 11 did not produce any hemolysin δ against 6 out of 134 isolated during acute infections, objectivizing a statistical significant connection between deficiency in hemolysin δ and chronic infections in a univariate analysis (p=0.001). Also, multi-variate statistical analysis finds this connection between a lack of hemolysin δ and chronicity of the infection, MSSA (p=0.023) and for MRSA (p=0.082). Conversely, no link between the absence of detection of the hemolysin and the presence of implantable devices could be found (p=0.470).

vii. Connection with GISA

Search for GISA was carried out with phenotype methods on the 168 prospectively collected strains. Five proved to be GISA and 4 of these 5 strains did not have any peak at 3005±5 Th and at 3035±5 Th (δ−). Considering the small number of GISA strains obtained in this study, a collection of 28 GISA strains perfectly characterized by the <<Centre National de Reference des Staphylocoques>> was analyzed with regard to their production of hemolysin δ. Nine strains out of 28 were δ− against 13/163 non-GISA strains from the clinical study, there again confirming the link between dysfunction of the agr system and the GISA resistance phenotype (p=0.001).

REFERENCES

Balaban, N. and R. P. Novick (1995). "Translation of RNAIII, the *Staphylococcus aureus* agr regulatory RNA molecule, can be activated by a 3'-end deletion." *FEMS Microbiol Lett* 133(1-2): 155-161.

Bittar, F., Z. Ouchenane, et al. (2009). "MALDI-TOF-MS for rapid detection of staphylococcal Panton-Valentine leukocidin." *Int J Antimicrob Agents* 34(5): 467-470.

Bizzini, A. and G. Greub (2010). "Matrix-assisted laser desorption ionization time-of-flight mass spectrometry, a revolution in clinical microbial identification." *Clin Microbiol Infect* 16(11): 1614-1619.

Boles, B. R. and A. R. Horswill (2008). "Agr-mediated dispersal of *Staphylococcus aureus* biofilms." *PLoS Pathog* 4(4): e1000052. Brunskill, E. W. and K. W. Bayles (1996). "Identification and molecular characterization of a putative regulatory locus that affects autolysis in *Staphylococcus aureus*." *J Bacteriol* 178(3): 611-618.

Cherkaoui, A., J. Hibbs, et al. (2010). "Comparison of two matrix-assisted laser desorption ionization-time of flight mass spectrometry methods with conventional phenotypic identification for routine identification of bacteria to the species level." *J Clin Microbiol* 48(4): 1169-1175.

Dauwalder, O., E. Carbonnelle, et al. (2010). "Detection of Panton-Valentine toxin in *Staphylococcus aureus* by mass spectrometry directly from colony: time has not yet come." *Int J Antimicrob Agents* 36(2): 193-194.

Dufour, P., S. Jarraud, et al. (2002). "High genetic variability of the agr locus in *Staphylococcus* species." *J Bacteriol* 184(4): 1180-1186.

Edwards-Jones, V., M. A. Claydon, et al. (2000). "Rapid discrimination between methicillin-sensitive and methicillin-resistant *Staphylococcus aureus* by intact cell mass spectrometry." *J Med Microbiol* 49(3): 295-300.

Felden, B., F. Vandenesch, et al. (2011). "The *Staphylococcus aureus* RNome and its commitment to virulence." *PLoS Pathog* 7(3): e1002006.

Figueiredo, A. M., S. Jarraud, et al. (2000). "Direct Submission." 2000, from http://www.ncbi.nlm.nih.gov/protein/AAG03054.1.

Fitton, J. E., A. Dell, et al. (1980). "The amino acid sequence of the delta haemolysin of *Staphylococcus aureus*." *FEBS Lett* 115(2): 209-212.

Fowler, V. G., Jr., G. Sakoulas, et al. (2004). "Persistent bacteremia due to methicillin-resistant *Staphylococcus aureus* infection is associated with agr dysfunction and low-level in vitro resistance to thrombin-induced platelet microbicidal protein." *J Infect Dis* 190(6): 1140-1149.

Goerke, C., S. Campana, et al. (2000). "Direct quantitative transcript analysis of the agr regulon of *Staphylococcus aureus* during human infection in comparison to the expression profile in vitro." *Infect Immun* 68(3): 1304-1311.

Hawkins, C., J. Huang, et al. (2007). "Persistent *Staphylococcus aureus* bacteremia: an analysis of risk factors and outcomes." *Arch Intern Med* 167(17): 1861-1867.

Kornblum, J. S., S. J. Projan, et al. (1988). "A rapid method to quantitate non-labeled RNA species in bacterial cells." *Gene* 63(1): 75-85.

Kreger, A. S., K. S. Kim, et al. (1971). "Purification and properties of staphylococcal delta hemolysin." *Infect Immun* 3(3): 449-465.

Otto, M. (2010). "Basis of virulence in community-associated methicillin-resistant *Staphylococcus aureus*." *Annu Rev Microbiol* 64: 143-162.

Otto, M. and F. Gotz (2000). "Analysis of quorum sensing activity in staphylococci by RP-HPLC of staphylococcal delta-toxin." *Biotechniques* 28(6): 1088, 1090, 1092, 1096.

Paizs, B. and S. Suhai (2005). "Fragmentation pathways of protonated peptides." *Mass Spectrom Rev* 24(4): 508-548.

Rose, W. E., M. J. Rybak, et al. (2007). "Correlation of vancomycin and daptomycin susceptibility in *Staphylococcus aureus* in reference to accessory gene regulator (agr) polymorphism and function." *J Antimicrob Chemother* 59(6): 1190-1193.

Sakoulas, G., G. M. Eliopoulos, et al. (2005). "Reduced susceptibility of *Staphylococcus aureus* to vancomycin and platelet microbicidal protein correlates with defective autolysis and loss of accessory gene regulator (agr) function." *Antimicrob Agents Chemother* 49(7): 2687-2692.

Sakoulas, G., G. M. Eliopoulos, et al. (2002). "Accessory gene regulator (agr) locus in geographically diverse *Staphylococcus aureus* isolates with reduced susceptibility to vancomycin." *Antimicrob Agents Chemother* 46(5): 1492-1502.

Sakoulas, G., H. S. Gold, et al. (2006). "Effects of prolonged vancomycin administration on methicillin-resistant *Staphylococcus aureus* (MRSA) in a patient with recurrent bacteraemia." *J Antimicrob Chemother* 57(4): 699-704.

Schweizer, M. L., J. P. Furuno, et al. (2011). "Increased mortality with accessory gene regulator (agr) dysfunction in *Staphylococcus aureus* among bacteremic patients." *Antimicrob Agents Chemother* 55(3): 1082-1087.

Somerville, G. A., A. Cockayne, et al. (2003). "Synthesis and deformylation of *Staphylococcus aureus* delta-toxin are linked to tricarboxylic acid cycle activity." *J Bacteriol* 185 (22): 6686-6694.

Szabados, F., K. Becker, et al. (2011). "The matrix-assisted laser desorption/ionisation time-of-flight mass spectrometry (MALDI-TOF MS)-based protein peaks of 4448 and 5302 Da are not associated with the presence of Panton-Valentine leukocidin." *Int J Med Microbiol* 301(1): 58-63.

Tholey, A. and E. Heinzle (2006). "Ionic (liquid) matrices for matrix-assisted laser desorption/ionization mass spectrometry-applications and perspectives." *Anal Bioanal Chem* 386(1): 24-37.

Welker, M. and E. R. Moore (2011). "Applications of whole-cell matrix-assisted laser-desorption/ionization time-of-flight mass spectrometry in systematic microbiology." *Syst Appl Microbiol* 34(1): 2-11.

Wertheim, H. F., D. C. Melles, et al. (2005). "The role of nasal carriage in *Staphylococcus aureus* infections." *Lancet Infect Dis* 5(12): 751-762.

```
                        SEQUENCE LISTING

<160> NUMBER OF SEQ ID NOS: 2

<210> SEQ ID NO 1
<211> LENGTH: 26
<212> TYPE: PRT
<213> ORGANISM: Staphylococcus aureus
<220> FEATURE:
<221> NAME/KEY: MISC_FEATURE
<222> LOCATION: (1)..(1)
<223> OTHER INFORMATION: Xaa is a N-terminal formylated methionine

<400> SEQUENCE: 1

Xaa Ala Gln Asp Ile Ile Ser Thr Ile Gly Asp Leu Val Lys Trp Ile
1               5                   10                  15

Ile Asp Thr Val Asn Lys Phe Thr Lys Lys
            20                  25

<210> SEQ ID NO 2
<211> LENGTH: 26
<212> TYPE: PRT
<213> ORGANISM: Staphylococcus aureus
<220> FEATURE:
<221> NAME/KEY: MISC_FEATURE
<222> LOCATION: (1)..(1)
<223> OTHER INFORMATION: Xaa is a N-terminal formylated methionine

<400> SEQUENCE: 2

Xaa Ala Gln Asp Ile Ile Ser Thr Ile Ser Asp Leu Val Lys Trp Ile
1               5                   10                  15

Ile Asp Thr Val Asn Lys Phe Thr Lys Lys
            20                  25
```

Traber, K. and R. Novick (2006). "A slipped-mispairing mutation in AgrA of laboratory strains and clinical isolates results in delayed activation of agr and failure to translate delta- and alpha-haemolysins." *Mol Microbiol* 59(5): 1519-1530.

Traber, K. E., E. Lee, et al. (2008). "agr function in clinical *Staphylococcus aureus* isolates." *Microbiology* 154(Pt 8): 2265-2274.

Tsuji, B. T., R. D. Maclean, et al. (2011). "Impact of accessory gene regulator (agr) dysfunction on vancomycin pharmacodynamics among Canadian community and healthcare associated methicillin-resistant *Staphylococcus aureus*." *Ann Clin Microbiol Antimicrob* 10: 20.

Turner, W. H. (1978). "Purification and characterization of an immunologically distinct delta-hemolysin from a canine strain of *Staphylococcus aureus*." *Infect Immun* 20(2): 485-494.

Verdon, J., N. Girardin, et al. (2009). "delta-hemolysin, an update on a membrane-interacting peptide." *Peptides* 30(4): 817-823.

Vuong, C., H. L. Saenz, et al. (2000). "Impact of the agr quorum-sensing system on adherence to polystyrene in *Staphylococcus aureus*." *J Infect Dis* 182(6): 1688-1693.

The invention claimed is:

1. A method for studying a sample containing a bacterial population of *Staphylococcus aureus* by a mass spectrometry technique comprising the following steps:
   a) placing the sample in contact with the medium allowing ionization by action of a laser beam of the molecules present in the sample,
   b) ionizing the molecules present in the sample by means of a laser beam,
   c) accelerating the ionized molecules obtained by a potential difference,
   d) letting the ionized and accelerated molecules freely move in at least one tube under reduced pressure,
   e) detecting at least one portion of the ionized and accelerated molecules which have freely moved, so as to measure the time they took for covering at least one tube under reduced pressure and for obtaining a signal corresponding to the number of detected ionized molecules at a given instant,
   f) calculating the mass over charge ratio [m/z] of the detected molecules, so as to obtain a signal corresponding to the number of ionized molecules of a same mass over charge ratio [m/z], depending on the m/z ratio of the detected molecules,
   g) determining either directly or indirectly whether the ionized molecules obtained in step b), there were or not ionized molecules of a mass/charge ratio [m/z] equal to 3005±5 Th or equal to 3035±5 Th, h) issuing a decision conditioned by the results obtained in step g).

2. The method according to claim 1, characterized in that step h) corresponds to a step of correlation of the absence of both ionized molecules with m/z equal to 3005±5 Th and ionized molecules of m/z equal to 3035±5 Th with the absence of hemolysin 6 and of its variant G10S in the analyzed bacterial population of *Staphylococcus aureus*.

3. The method according to claim 1, characterized in that the step h) corresponds to a step of correlation of the absence of both ionized molecules with m/z equal to 3005±5 Th and ionized molecules of m/z equal to 3035±5 Th with a dysfunction of the agr (<<Accessory Gene Regulator>>) system in the analyzed bacterial population of *Staphylococcus aureus*.

4. The method according to claim 1, characterized in that the analyzed bacterial population of *Staphylococcus aureus* comes from a biological sample from a patient and in that step h) corresponds to a step for correlation of the absence of both ionized molecules with m/z equal to 3005±5 Th and ionized molecules of m/z equal to 3035±5 Th with issuance for said patient of a clinical diagnostic known to be related to the dysfunction of the agr system.

5. The method according to claim 1, characterized in that the analyzed bacterial colony of *Staphylococcus aureus* stems from a biological sample from a patient and in that step h) corresponds to a step for correlation of the absence of both ionized molecules with m/z equal to 3005±5 Th and ionized molecules of m/z equal to 3035±5 Th with the diagnostic of a chronic infection in a patient.

6. The method according to claim 1, characterized in that step h) corresponds to a step for correlation of the absence of both ionized molecules of m/z equal to 3005±5 Th and ionized molecules of m/z equal to 3035±5 Th with a classification of the analyzed bacterial *Staphylococcus aureus* population as having the risk of exhibiting reduced sensitivity to glycopeptides (i.e. GISA).

7. The method according to claim 1, characterized in that mass spectrometry is carried out on a sample containing a population from 10 to $10^9$ bacteria, and preferably from $10^5$ to $10^6$ bacteria.

8. The method according to claim 1, characterized in that the mass spectrometry used is mass spectrometry (MS) with matrix-assisted desorption-ionization and measurement of the time of flight (MALDI-TOF).

9. The method according to claim 8 characterized in that the determination of step g) is directly inferred from the presence on the obtained mass spectrum of a peak with an m/z value equal to 3005±5 Th or to 3035±5 Th or from the absence of peaks both at 3005±5 Th and at 3035±5 Th.

10. The method according to claim 1, characterized in that the mass spectrometry used is MALDI TOF/TOF mass spectrometry.

11. The method according to claim 10, characterized in that in step d), the ionized molecules are left to move in a first tube under reduced pressure, the ions with an m/z mass equal to 3005±5 Th and/or with a m/z mass equal to 3035±5 Th are selected, the ionized molecules after their fragmentation are again accelerated, and the, either fragmented or not, ionized molecules are left to freely move in a second tube.

12. The method according to claim 10, characterized in that the determination of step g) is indirectly inferred from the presence of at least five fragments from the following ion fragments y and b:

the ion fragments y with masses 147.113, 275.208, 376.255, 523.324, 651.419, 765.462, 864.530, 965.578, 1080.605, 1193.689, 1306.773, 1492.852, 1620.947, 1720.016, 1833.100, 1948.127, 2005.148, 2118.232, 2219.280, 2306.312, 2419.396, 2532.480, 2647.507, 2775.565, 2846.603 and 2976.635; and ion fragments b of masses 131.040, 202.077, 330.136, 445.163, 558.247, 671.331, 758.363, 859.410, 972.494, 1029.516, 1144.543, 1257.627, 1356.695, 1484.790, 1670.870, 1783.954, 1897.038, 2012.065, 2113.112, 2212.181, 2326.224, 2454.319, 2601.387, 2702.435, 2830.530 and 2958.625, with a tolerance of ±1.5 Th, for the peak at 3005±5 Th, and/or the ion fragments y of masses 147.113, 275.208, 376.255, 523.324, 651.419, 765.462, 864.530, 965.578, 1080.605, 1193.689, 1306.773, 1492.852, 1620.947, 1720.016, 1833.100, 1948.127, 2035.159, 2148.243, 2249.290, 2336.322, 2449.406, 2562.491, 2677.517, 2805.576, 2876.613 and 3006.646; and the ion fragments b of masses 131.040, 202.077, 330.136, 445.163, 558.247, 671.331, 758.363, 859.410, 972.494, 1059.526, 1174.553, 1287.638, 1386.706, 1514.801, 1700.880, 1813.964, 1927.048, 2042.075, 2143.123, 2242.191, 2356.234, 2484.329, 2631.398, 2732.445, 2860.540 and 2988.635, with a tolerance of ±1.5 Th, for the peak at 3035±5 Th.

13. The method according to claim 1, characterized in that the medium with which the sample is put into contact corresponds to a matrix suitable for MALDI MS deposited on a target, and in that the method includes before step b), the obtaining of crystallization of the matrix on or in which the molecules of the sample are adsorbed.

14. The method according to claim 13, characterized in that the matrix contains a compound selected from 3,5-dimethoxy-4-hydroxycinnamic acid, α-cyano-4-hydroxycinnamic acid, ferulic acid and 2,5-dihydroxybenzoic acid.

* * * * *